United States Patent
Altosaar et al.

(10) Patent No.: US 10,294,268 B2
(45) Date of Patent: May 21, 2019

(54) METHODS FOR SEPARATING AND PURIFYING ENDOGENOUS, EXOGENOUS AND RECOMBINANT PROTEINS/PEPTIDES FROM PLANTS AND ANIMALS USING AQUEOUS-FREE, ANHYDROUS STRATEGIES

(71) Applicant: Proteins Easy Corp., Ottawa (CA)

(72) Inventors: Illimar Altosaar, Ottawa (CA); Trevor Greenham, Ottawa (CA)

(73) Assignee: PROTEINS EASY CORP., Ottawa (CA)

( * ) Notice: Subject to any disclaimer, the term of this patent is extended or adjusted under 35 U.S.C. 154(b) by 300 days.

(21) Appl. No.: 15/027,884

(22) PCT Filed: Oct. 9, 2014

(86) PCT No.: PCT/US2014/059808
§ 371 (c)(1),
(2) Date: Apr. 7, 2016

(87) PCT Pub. No.: WO2015/054444
PCT Pub. Date: Apr. 16, 2015

(65) Prior Publication Data
US 2016/0251396 A1    Sep. 1, 2016

Related U.S. Application Data

(60) Provisional application No. 61/887,986, filed on Oct. 8, 2013.

(51) Int. Cl.
| *A61K 38/01* | (2006.01) |
| *C07K 1/00* | (2006.01) |
| *C07K 14/00* | (2006.01) |
| *C07K 16/00* | (2006.01) |
| *C07K 17/00* | (2006.01) |
| *C07K 1/36* | (2006.01) |
| *C07K 1/12* | (2006.01) |
| *C07K 1/14* | (2006.01) |

(52) U.S. Cl.
CPC .............. *C07K 1/36* (2013.01); *C07K 1/12* (2013.01); *C07K 1/122* (2013.01); *C07K 1/145* (2013.01)

(58) Field of Classification Search
CPC .......... C07K 1/12; C07K 1/122; C07K 1/145; C07K 1/36
See application file for complete search history.

(56) References Cited

U.S. PATENT DOCUMENTS

| 5,521,097 A * | 5/1996 | Uchida ................. C07K 1/128 436/173 |
| 6,072,039 A * | 6/2000 | Haase ................. C07K 14/675 435/69.7 |
| 7,135,619 B1 | 11/2006 | Visser et al. |
| 2003/0148453 A1 * | 8/2003 | Mantyla .............. C12N 9/2434 435/69.1 |
| 2012/0220482 A1 | 8/2012 | Moola et al. |
| 2015/0342224 A1 | 12/2015 | Medoff |

FOREIGN PATENT DOCUMENTS

| CA | 529624 A | 8/1956 |
| CN | 102076741 B | 4/2013 |

OTHER PUBLICATIONS

Gu et al. "Selective Gas-Phase Cleavage at the Peptide Bond C-Terminal to Aspartic Acid in Fixed-Charge Derivatives of Asp-Containing Peptides". Anal. Chem. 72:5804-5813. (Year: 2000).*
Miyatake et al. "Specific Chemical Cleavage of Asparaginyl and Glycyl-Glycine Bonds in Peptides and Proteins by Anhydrous Hydrazine Vapor". J. Biochem. 115:208-212 (Year: 1994).*
Honegger et al. "Chemical modification of peptides by hydrazine" Biochem. J. 199:53-59. (Year: 1981).*
International Search Report and Written Opinion issued in PCT/US2014/059808 dated Feb. 10, 2015.
GenBank AAL02331.2.
International Preliminary Report on Patentability (Chapter 1) issued in PCT/US2014/059808 dated Apr. 12, 2016.
Kim et al., "Effect of heating temperature on particle size distribution in hard and soft wheat flour," Journal of Cereal Science, 2004, pp. 9-16, vol. 40.
Lee et al., "Effect of Particle Size on the Solubility and Dispersibility of Endosperm, Bran, and Husk Powders of Rice," Food Science and Biotechnology, 2008, pp. 833-838, vol. 17, No. 4.
Peters et al., "Efficient recovery of recombinant proteins from cereal endosperm is affected by interaction with endogenous storage proteins," Biotechnology Journal, 2013, pp. 1203-1212, vol. 8.
Stoddard, "Survey of Starch Particle-Size Distribution in Wheat and Related Species," Cereal Chemistry, 1999, pp. 145-149, vol. 76, No. 1.

\* cited by examiner

*Primary Examiner* — Zachary J Miknis
(74) *Attorney, Agent, or Firm* — Arent Fox LLP

(57) ABSTRACT

The present invention relates to recombinant proteins/peptides from plant and animal materials, compositions comprising the proteins/peptides and methods for making them.

15 Claims, 13 Drawing Sheets

Figure 1:
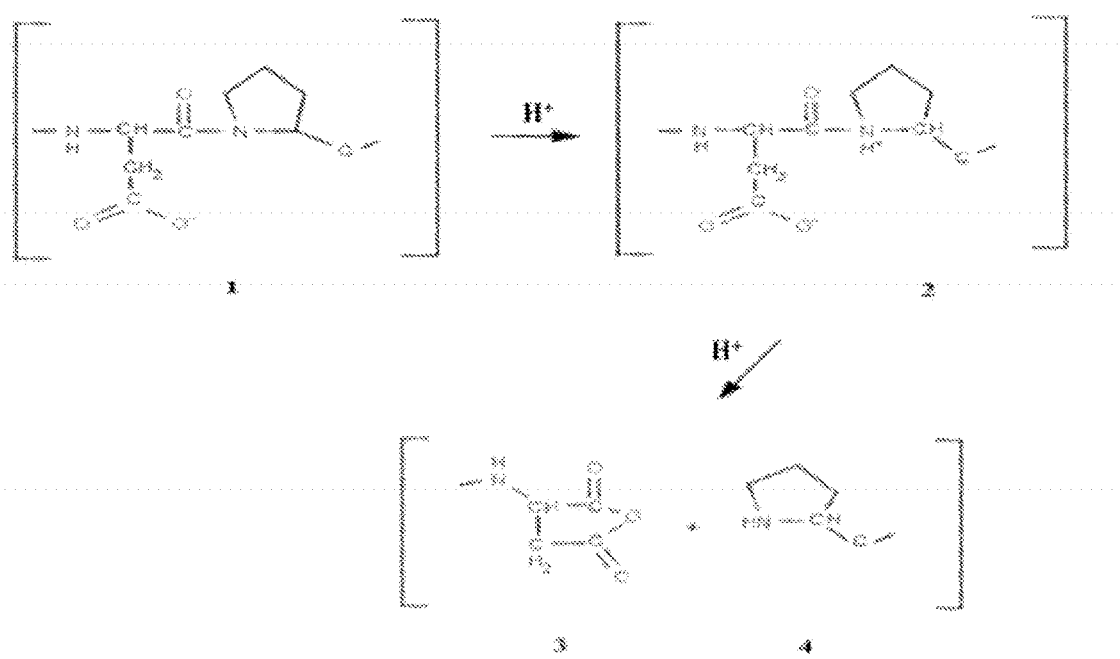
Figure 2:
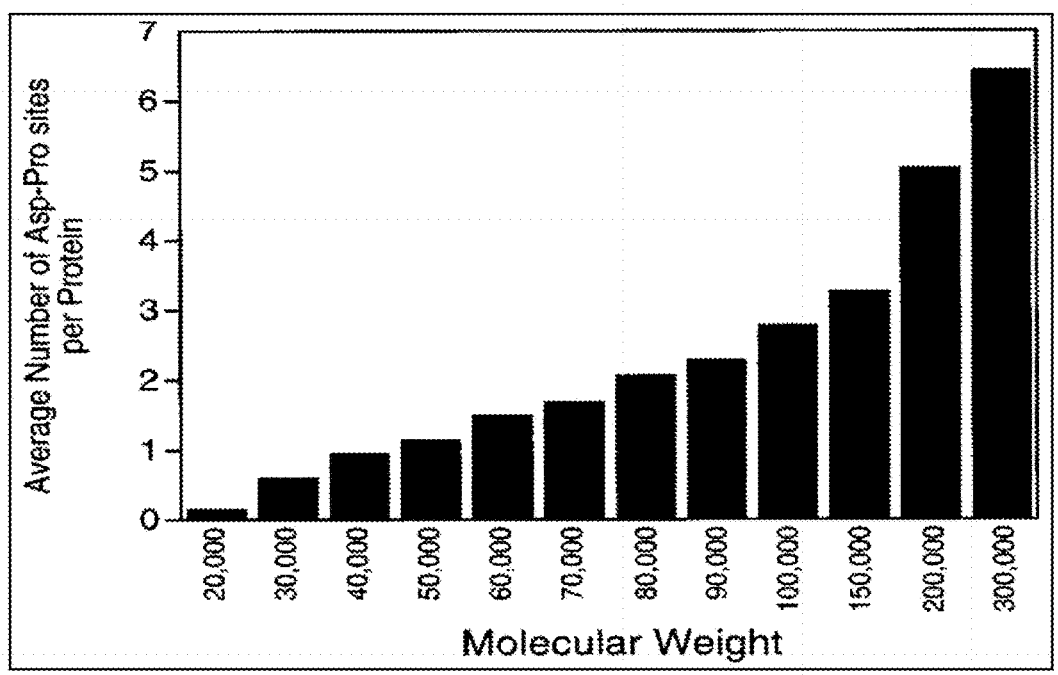
Figure 3:
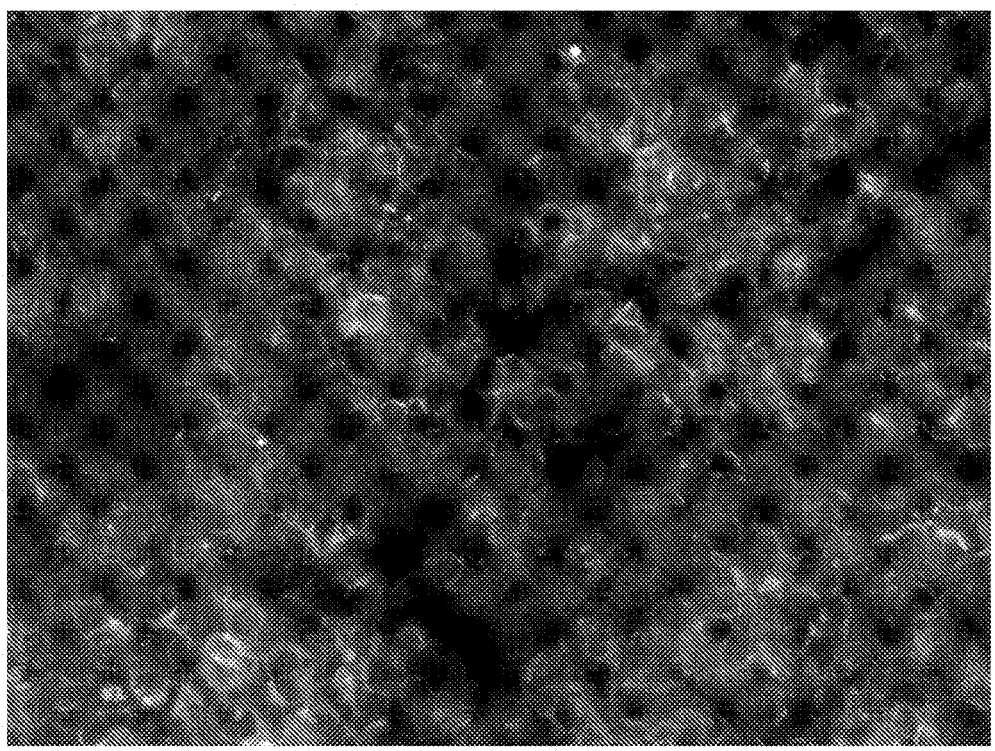

Figure 11 starch granules in gas flow

PHA carrier protein domain remains tethered on granules

Dry fission of Asp-Pro peptide bonds

Protein of interest is liberated into the gas flow to be trapped in dust collector or liquid bubble trap

METHODS FOR SEPARATING AND PURIFYING ENDOGENOUS, EXOGENOUS AND RECOMBINANT PROTEINS/PEPTIDES FROM PLANTS AND ANIMALS USING AQUEOUS-FREE, ANHYDROUS STRATEGIES

CROSS-REFERENCE TO RELATED APPLICATIONS

This application is a National Stage entry of International Application No. PCT/US2014/059808, filed Oct. 9, 2014, which claims the benefit of priority to U.S. Provisional Application No. 61/887,986, filed Oct. 8, 2013. The disclosures of the prior applications are hereby incorporated in their entirety by reference.

FIELD OF THE INVENTION

The present invention relates to recombinant proteins/peptides from plant and animal materials, compositions comprising the proteins/peptides and methods for making them.

BACKGROUND OF THE INVENTION

Biopharmaceuticals are the fastest growing sector within the pharmaceutical industry, with a U.S. market value of $120 billion in 2009. These proteins/peptides are mainly produced using recombinant technology and established production platforms such as microbial, yeast, or mammalian cell cultures. The effectiveness of different platforms is judged primarily on protein yield, posttranslational modifications, ease of downstream purification and the capital requirements needed for commercialization. *E. coli* was the first large-scale protein production host and has several advantages such as cheap fermentation runs, short generation times and high titers of recombinant protein.

Mammalian cultures (CHO cells predominantly) were introduced to overcome some of the shortfalls of the microbial expression platforms such as the formation of inclusion bodies upon high titers, difficulty in purification due to endogenous endotoxin contaminants, and most importantly microbes' lack of eukaryotic posttranslational modifications (glycosylation, acylation, disulphide bridge formation etc.) which are often required for protein folding and function. CHO cells can produce recombinant proteins with glyco-profiles similar to those of native proteins. Innovations in target-gene insertion, culture media manipulation and apoptosis inhibition have improved titers to over 5 g/L.

Currently, CHO cells are the most utilized production platform despite their high infrastructure and process costs. The rapidly growing demand for biologics of all types has caused extreme shortages in manufacturing capacity. By creating a few successful biologics, the pharmaceutical industry has heightened the public need for a greater supply of additional useful protein drugs and protein agents. The high capital requirements related with the aforementioned platforms has restricted the supply of biopharmaceuticals, prompting other production strategies to be investigated for improved economics and improved capacity.

With the advent of plant transformation technology, plants and algae have proven to be feasible bioreactors for the large-scale production of recombinant proteins. The advantages are in terms of production costs, scalability and product safety, case of storage and distribution, none of which can be matched by any current bacterial or mammalian production platform. Despite the compelling advantages, several molecular pharming initiatives have fallen short primarily due to the high costs associated with the downstream purification processes. These processes rely heavily on aqueous chromatographic technology, and can account for over 70% of the total operational costs. In addition to the operational costs, there are also issues with contamination, product degradation via proteases, and large amounts of waste produced as a byproduct of aqueous recombinant protein purification. For example, even when commercial protein is expressed in seed endosperm as a non-targeted foreign protein and left to its own devices, the protein-of-interest is often trapped in undesirable protein-protein interactions with host proteome components. See, e.g. Peters et al., Efficient recovery of recombinant proteins from cereal endosperm is affected by interaction with endogenous storage proteins, *Biotechnology Journal* 8, (10), 1203-1212, October 2013.

Therefore, a purification process that is cheap, clean and safe is needed to overcome the significant shortfalls found in conventional aqueous purification strategies. The invention described herein solves the limitations of current aqueous purification methods by first pinning or tethering the protein onto the surface of a cellular particle such as starch granule, a particle that is then isolated to a dry state followed by cleavage of the fusion protein employing an anhydrous method. The technology eliminates product loss due to proteolytic degradation; the dry environment prevents bacterial or pathogen contaminations, and drastically reduces the amount of environmentally harmful buffers and reagents typically used for aqueous recombinant protein purification. The novel functionalized particle bearing the protein of interest can be deployed directly or further cleaved to liberate the protein of interest, freed of its carrier domain and carrier particle.

Selective chemical cleavage has proven to be a useful way to identify proteins by observing their subsequent cleavage patterns. In 1953, there was a report of selective bond cleavages for peptides that contained serine, threonine, and glycine residues when exposed to hydrochloric acid at room temperature. The cleavages at the N-terminal of the serine and threonine followed a mechanism involving a N→O shift of hydroxyl groups. The first selective cleavage at aspartic residues was observed in 1950 when a protein was heated and incubated in a weak acid solution. This caused cleavage at aspartic and asparagine residues.

In 1993, a specific and very facile cleavable bond was observed in the gas phase. This bond was the Asp-Pro peptide bond, and is much more unstable than any other bond. The mechanism of cleavage between this peptide bond is facile due to the presence of a labile proton on the side chain of aspartic acid along with the basicity of the downstream proline. The labile proton found in the side chain of the aspartic acid is important for cleavage as its esterification inhibited cleavage. The Asp-Pro bond can be cleaved under conditions where all other peptide bonds are stable. Furthermore, the Asp-Pro pairing is amongst the rarest of all amino acid pairs found in nature. The distinct properties of the Asp-Pro bond and its rarity in peptides and proteins, makes it an ideal gas-phase cleavable linker.

SUMMARY OF INVENTION

The invention described herein provides a method for the separation and purification of proteins/peptides from cellular material, whether the proteins/peptides are endogenous, exogenous or recombinant. The invention is based on gas-phase cleavage chemistry, allowing separation and purification of proteins/peptides anhydrously from dried cellular material derived from any living organism. Knowing that gas-phase cleavage has been used in solid-phase protein sequenators to preferentially liberate the N-terminal phenyl-thiohydantoin amino acid residue, we reasoned that gas-phase cleavage of protein/peptide bonds could be deployed to release proteins/peptides directly from dried biological material.

In various embodiments, the invention described provides a method or process for the separation and purification of recombinant proteins/peptides from cellular material, based on the utilization of cleavable gas-phase peptide linker sequences. Fusion proteins present in dried biological material containing said gas-phase linkers can be separated and purified from dry biological material using gas-phase chemistry.

In some specific embodiments, the gas-phase linker sequence is located in the fusion protein/peptide where cleavage of said linker releases the recombinant protein of interest in to the air-flow from its fusion partner. This recombinant protein is collected in high purity by passing the air-flow through a collection chamber or protein/peptide trap. The invention represents an economic and scalable way of recombinant protein separation and purification, as well as an anhydrous protein/peptide screening method that can be used to separate, isolate and identify proteins/peptides without requiring aqueous buffers or reagents.

In various embodiments, the invention provides a scalable, cost effective anhydrous strategy for the purification of recombinant proteins from any transformed biological material. Traditional protein purification strategies from biological feedstock usually include a means of grinding, breaking, pulverizing or disrupting the cells of the production organism, and use of an aqueous, buffered extraction medium. The biological extracts are then separated into fractions (for example by centrifugation or sedimentation) and the recombinant protein is further purified using several steps of chromatography. In one specific embodiment the invention provides a method for utilizing the protein of interest while it still remains tethered or attached to the cellular carrier particles, having been rendered as novel functionalized particles.

In another embodiment, recombinant proteins are recovered from the surface of any cellular organelle or structural component (e.g., glycogen granule, starch granule, protein body, cell wall, chloroplast membrane, flagella) comprising the step of incubating the desiccated or dried biological material with a suitable gaseous cleavage reagent.

In such embodiment, the recombinant protein is expressed as a fusion protein, consisting of a carrier fragment and a second element, either upstream or downstream, encoding the protein of interest separated by a peptide linker site susceptible to cleavage in the gas phase. A specific area for recombinant protein expression is within the seed, a dry environment nature has designed to accumulate and store proteins. In such case, a gas phase cleavable linker is selected from the group of Asp-Pro, Gly-Thr, Gly-Gly, Met, Scr, Trp, Asn-Gly with Asp-Pro being favored. The gaseous reagent used for cleavage of the -Asp-Pro- peptide linker is selected from the group consisting of gaseous heptafluorobutyric acid, acetic acid, formic acid, hydrochloric acid, anhydrous hydrazine, perfluorobutyric acid, trifluoroacetic acid, fluorosulfuric acid or perfluoric acid and mixtures thereof.

In another embodiment the method includes steps to isolate cellular organelles or structural components prior to incubation with the gaseous cleavage reagent. It also includes steps to capture the cleaved protein of interest in aqueous buffers, sterile water, on a dry filter, or in a protein/peptide dust trap.

The method provides a number of advantages over conventional recombinant protein purification strategies i.e., those that rely on aqueous buffers/reagents and chromatography. A critical advantage of dry purification is that it prevents product loss that usually occurs from proteolysis. Most known proteases are of aqueous cytoplasmic origin, and thus are only active in an aqueous environment, and inactive in low moisture environments. The anhydrous strategy eliminates the need for conventional bio-processing protease inhibitor cocktails and hundreds of thousands of liters of bio-waste that is produced from large scale aqueous purification strategies. Anhydrous purification can be accomplished at a fraction of the cost compared to the conventional aqueous strategies.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is an exemplary mechanism for one embodiment of the gas-phase decomposition of an Asp-Pro bond in a peptide with acid.

FIG. 2 is an example of the very limited biodiversity of the aspartyl-prolyl sequence in nature and its remarkable paucity thus making it a surprisingly useful cleavage site for dry fission of carrier element from protein-of-interest element. The average number of Asp-Pro bonds per protein is shown plotted versus molecular weight, using a database of known previously sequenced protein primary sequences.

FIG. 3 illustrates immunolocalization of puroindoline fusion proteins in rice seed according to one exemplary embodiment. The bright halos represent the fusion protein tethered onto starch granule surfaces.

FIG. 4 illustrates SDS-PAGE analysis of protein banding proteins of anhydrous cleavage of tyrosinase with gaseous trifluoroacetic acid (TFA) according to one exemplary embodiment. Identification of three anhydrous cleavage products indicated by arrows (right-hand lane), after 16 hours exposure of tyrosinase (80 kDa) to pure, gaseous TFA at room temperature by silver stained 15% SDS-PAGE gels, run at 120V for 2.5 hours. Tyrosinase unexposed to pure, gaseous TFA was used as a control (center lane). Aliquots were loaded such that each well contained 4 μg of protein, as determined by the Bradford protein concentration assay. Left lane represents 5 μl the PageRuler protein ladder, used as the molecular weight marker for control of relative mobility (Mr) of unknown proteins in the gel.

FIG. 5 illustrates immunodetection of puroindoline carrier element (PIN) in transgenic rice flour. Triton X-114 phase partitioning of protein extracts from wheat (positive control), transgenic PIN+ rice, and wild type rice cultivar Kaybonnet (negative control) were fractionated on a native PAGE gel. Separated proteins were transferred to a Nitrocellulose membrane and incubated with anti-PN primary antibody and anti-rabbit conjugated horseradish peroxidase secondary antibody. Lane (1) Mr Ladder, (2) wheat cultivar AC Barry PIN extract, (3) PIN+ rice extract, (4) wild type rice flour PIN extract.

Figure 6:
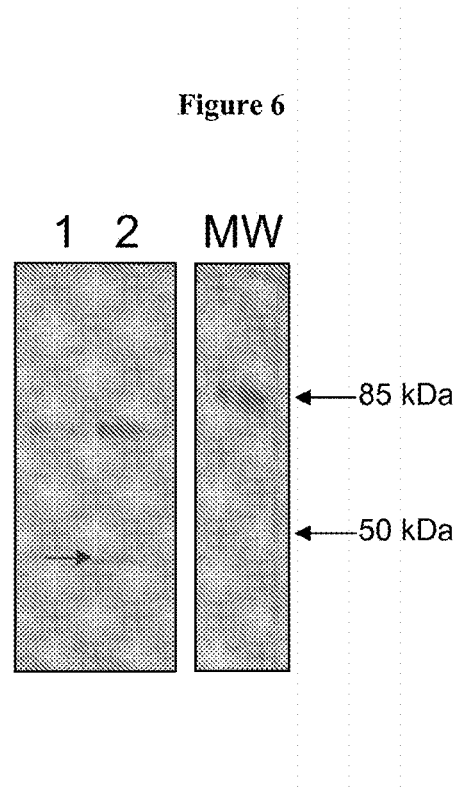

FIG. 6 illustrates SDS-PAGE of anhydrous cleavage of catalase with gaseous TFA. Catalase is a 72 kDa protein possessing at least one Asp-Pro cleavage site in its 527 residue amino acid sequence when isolated from Bos taurus. An Asp-Pro cleavage site in bovine catalase appears approximately in the middle of the amino acid sequence of catalase, therefore two cleavage products of similar sizes are predicted. The expected peptide sizes are 35 and 37 kDa, visualized as one band in a low resolution SDS-PAGE gel but can be resolved into two distinct bands in a high resolution gel. Photograph displays identification of two anhydrous cleavage products of similar mass represented by the red arrow (lane 2), after 16 hour exposure of catalase (72 kDa) to pure, gaseous TFA in air at room temperature by silver stained 15% SDS PAGE, run at 120V for 2.5 hours. Catalase unexposed to pure, gaseous TFA was used as a control (lane 1). Aliquots were loaded such that each well contains 4 µg of protein, as determined by Bradford assay. Lane MW represents 5 µl of the PageRuler protein ladder, used as the molecular weight marker.

Figure 7:
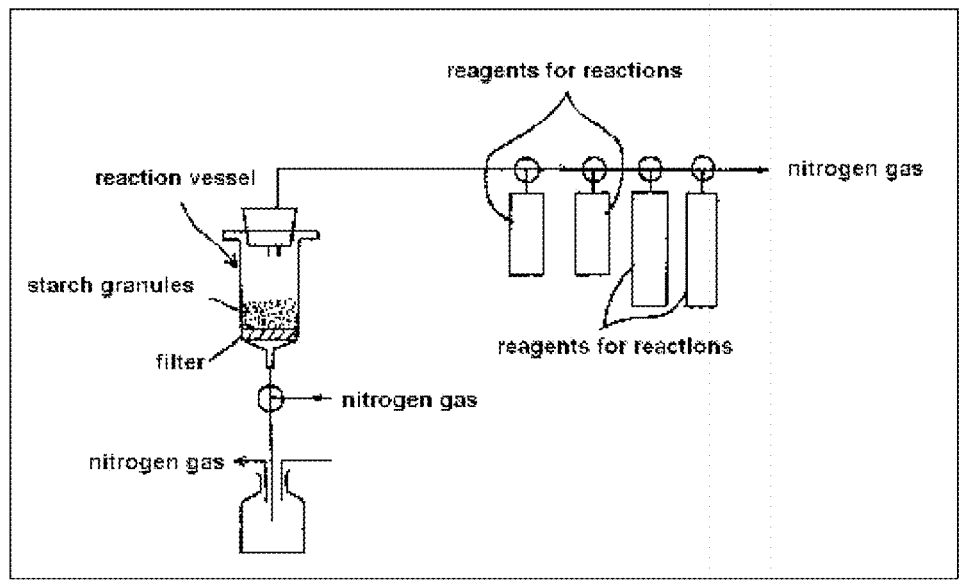

FIG. 7 illustrates a modified schematic diagram of an anhydrous cleavage apparatus for treating dry plant and animal particles with gases that preferentially cleave rare amino acid residue pairs in fusion proteins that are tethered to the particle by a carrier protein domain according to one embodiment.

Figure 8:
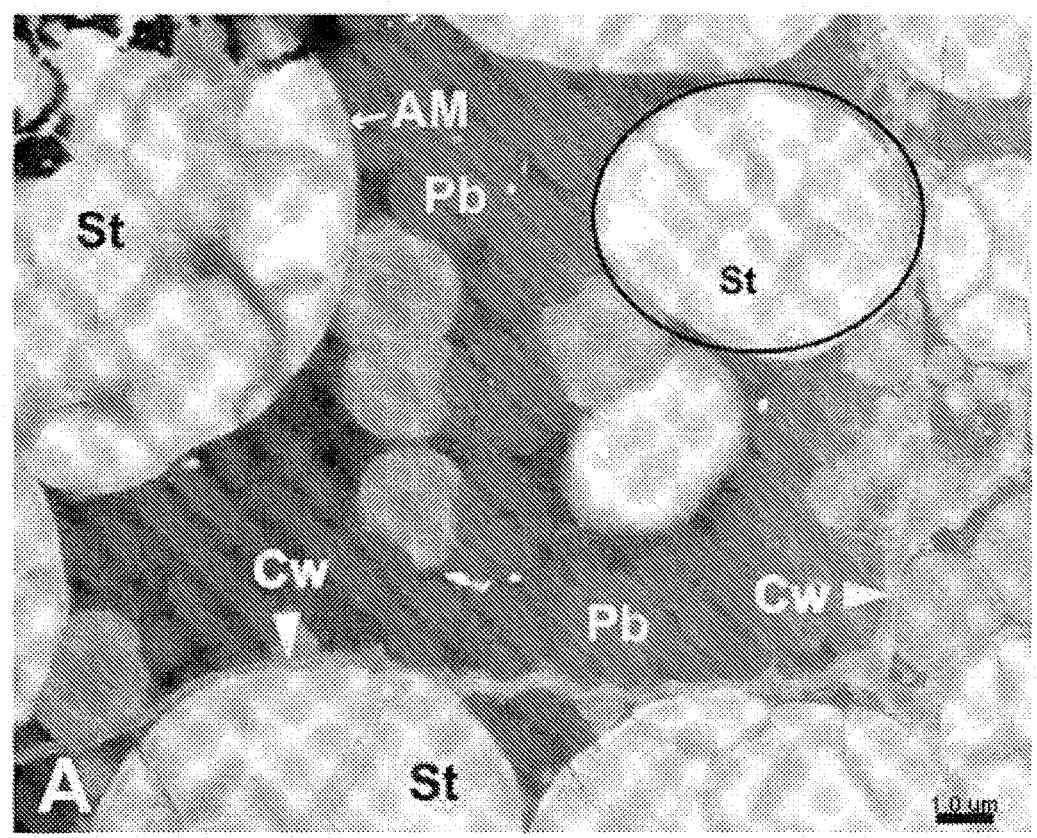

FIG. 8 illustrates rice starchy endosperm as viewed by a transmission electron micrograph. Starch granules (St), amyloplast membranes (AM), protein bodies (Pb), and cell walls (Cw) are the only components visible according to one embodiment. During endosperm maturation the other organelles such as Golgi, lysosomes, peroxisomes, and rER are digested via the Autophagy pathways. The upper right hand corner indicates the structure of a typical composite starch granule (circled) wherein aggregate the polyhedric individual sub-granules.

Figure 9:
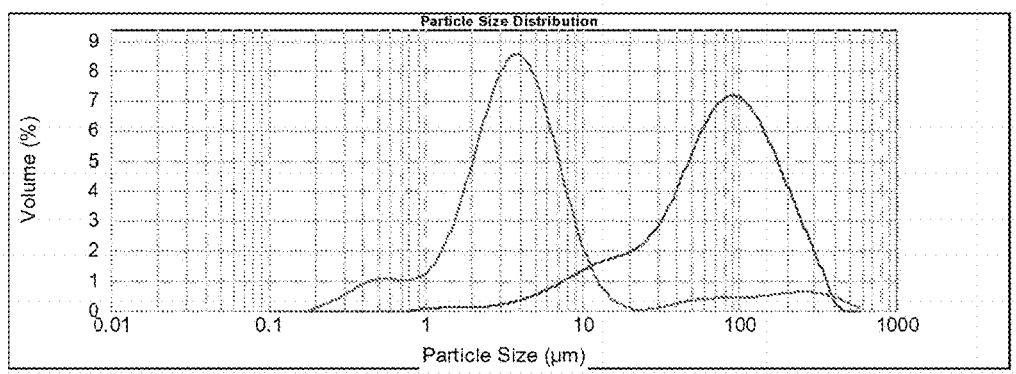

FIG. 9 illustrates particle size distribution of powdered and micronized rice flour after Matsubo elbow-jet air-classification according to one embodiment. The red line represents particle size distribution of milled rice flour and the green line represents the particle size distribution of milled and air-classified rice flour. There was no separation of particles (e.g. individual rice starch granules) after milling alone, but after the powder was air-classified a sharp peak at the expected position of starch granule size (4-6 µm) was observed.

Figure 10:
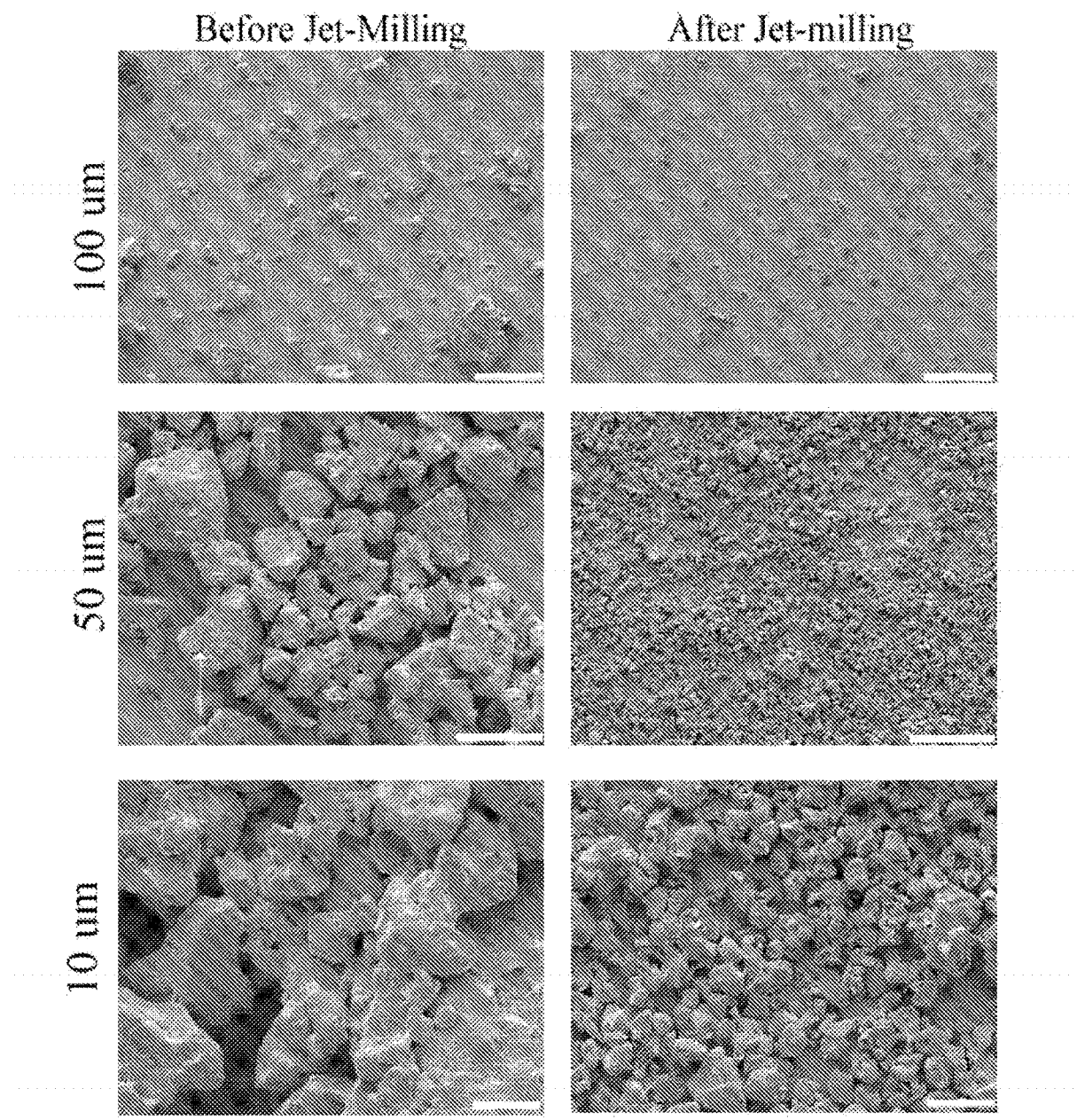

FIG. 10 illustrates a scanning electron micrograph (SEM) of rice powder before and after jet-milling according to one embodiment. Ninety micron wide particles predominate in Hammer Milled Powder (HMP) shown in left column panels labeled "Before Jet-milling" (top left panel, turquoise arrow) but were no longer observed in Jet Milled Powder (JMP) "After Jet-milling" column. Several HMP particles contain large fissures (left column, middle row panel, white arrow). Higher magnification images of HMP indicate the presence of a mosaic of <10 um wide particles held together (lower left panel).

FIG. 11 illustrates a process flow schematic diagram of the invention indicating turbulent dispersion of proteinated granules bearing recombinant protein contained inside a horizontal gas-phase cleavage flow according to one embodiment. The invention process can also be operated by placing the fluidized bed reactor or dispersion of particles into a vertical or angulated orientation, one wherein the particles do not clog the fritted glass discs retaining the proteinated granules in the gas-phase cleavage reactor bed or column.

Figure 12:
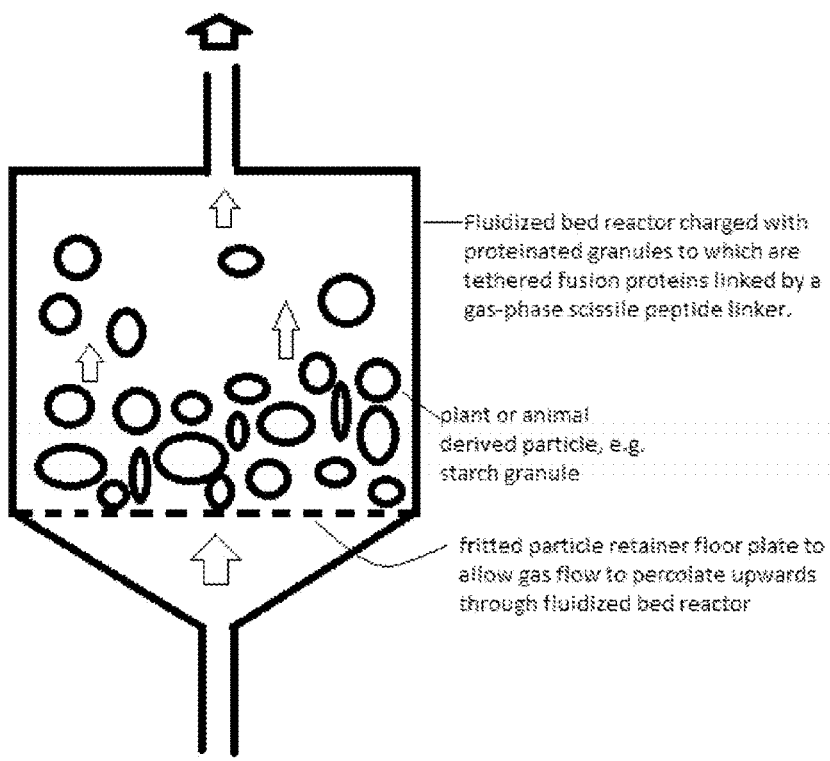

FIG. 12 illustrates a drawing of one possible configuration of the invention wherein dry animal or plant sourced particles are tumbled in an airflow in a manner similar to a lottery ball tumbler filled with ping-pong balls. In this rendition and embodiment, during Stage 1 the Protein-Easer™ performs aero-abrasion via particle-particle collision to release the untethered proteins from the particles (e.g. rice starch granules) into the air flow to remove the background protein matrix and host organism proteome mixture. Protein content of the exiting air by Near Infra-Red (NIR) or real-time spectral methods will indicate when all untethered proteins have been air-polished off the surface of the particles. When judged clean and free of non-recombinant proteins, then the carrier particles are ready for gas-phase cleavage treatment. By use of a valve at the inflow tube the air flow is switched over to a supply of air carrying in it a mixture of heptafluorobutyric acid or other gas-phase cleavage gas for anhydrous fission (breaking) of susceptible peptide bond(s) in the linker. In this way the dry recombinant protein-of-interest is liberated from the particle reactor bed, departing it via the exit flow tube indicated at the top of the model diagram. Such POI is trapped in dry or wet form, as the need be, using prior art dust collection technology.

Figure 13:
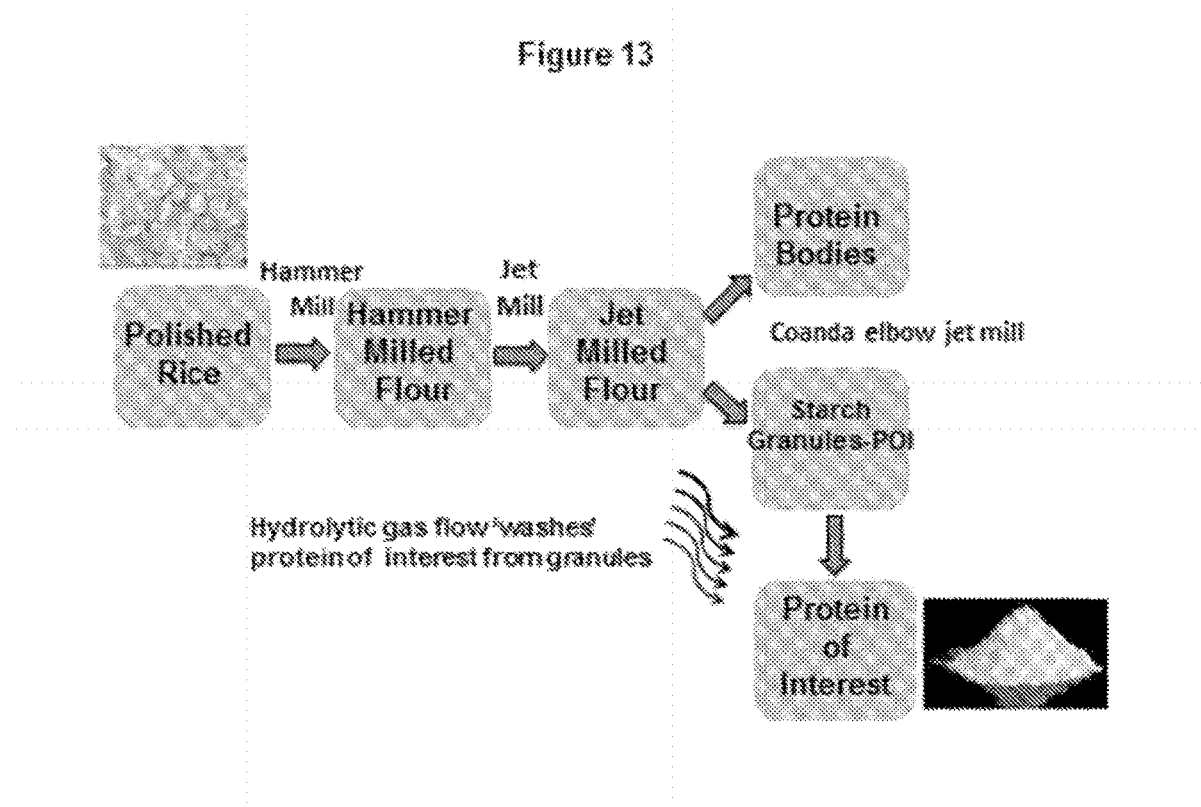

FIG. 13 illustrates how dry starch granules tethered with Protein of Interest are removed from transgenic rice kernels by successive comminution, subjected to hydrolytic gas flow cleavage, liberating protein of interest quickly, and in purified dry form. In one preferred embodiment of the process of the invention, endogenous, exogenous and recombinant proteins/peptides from plants and animals are separated and purified using aqueous-free, anhydrous strategies. Transgenic rice expressing commercial protein is harvested, polished, stored until needed, and hammer-milled, followed by jet milling, and elbow-jet milling (e.g. Matsubo 'Coanda' mill). Particle reduction and particle separation steps employ milling and air classification procedures known in the prior art and are easily adaptable to large-scale, custom-tailored specifications under GMP conditions. The final step of processing these proteinated granules uses gas phase fission whereby the Protein of Interest is separated quickly from the solid starch granule surface and purified in dry form using protein capture methods of powder entrapment filters, or if preferred, using sparging into sterile water or buffer.

DETAILED DESCRIPTION OF THE INVENTION

The present invention relates to novel methods for production of recombinant proteins and peptides that can be anhydrously purified from host cell components. DNA used for encoding the protein of interest may be all or part of a naturally occurring sequence; it may be a synthetic sequence or a combination of. The method relates to preparing an expression cassette which comprises a DNA sequence encoding a fusion carrier linked to a second DNA sequence encoding a gas-phase cleavable linker and fused to a third DNA sequence encoding the protein or peptide of interest. The chimeric DNA sequence will be ligated downstream of a promoter sequence of choice and ligated upstream of a terminator sequence of choice. This will depend on host cell, desired expression pattern, and final deposition of the expressed recombinant fusion protein to a location that is readily accessible by gas or vapors to ensure cleavage and separation of the protein or peptide of interest from the fusion carrier and host cell components.

The transformed host cells may be any source including but not limited to plants, algae, fungi, bacteria and animals. In this embodiment the host cells are of plant and algal origin, and the recombinant fusion protein is expressed and translocated to starch granules, cell wall, chloroplast membranes, protein body surfaces or on the surface of other subcellular organelles or structural components. In one specific embodiment, the translocation of the fusion protein will be to starch granules and cell wall. In one specific embodiment, in plants the recombinant fusion protein is expressed in the seed and localized onto the starch granule surfaces and in algae the recombinant fusion protein is expressed inside the chloroplast and localized to the starch granule surfaces.

One advantage of using seed based expression and the starch granule surface as a landing zone for our recombinant fusion proteins is that they can be easily isolated from host cell components using anhydrous methods such as milling, air-classification and air-cyclone technologies. In combination, these technologies can isolate starch granules from the other cellular components based on their size and density. These technologies are a fraction of the cost of aqueous based methods, and provide a dry environment where the recombinant fusion protein remains stable. There are a range of dry and wet milling techniques, but few of these reduce particles to the required size of <10 μm wide. The preferred technique preserves the rice powder in the dry state (i.e. <14% total moisture). Hammer-milling draws particles into its milling chamber by vacuum suction.

Once inside the chamber, high speed hammer arms fracture the rice particles. Rice particles remain in the chamber until reduced to the pore size of the exit sieve and are then drawn into a collection flask. This milling technique is effective at reducing rice to particles 100 μm wide, but readily clogs finer exit sieves. Jet-milling also uses air pressure to feed or drive the powder into the milling chamber, but rather than an exit sieve, jet-milling uses rapid directional changes in air-flow to retain unmilled particles. Air is injected tangentially to the wall of the cylindrical milling chamber. This jet of air drives the particles in the chamber to circulate rapidly around the chamber. The air is drawn radially to the centre of the chamber to an exit port. Particles in the chamber experience a drag force that is proportional to their cross-sectional area. If the particles do not possess sufficient momentum to continue on their circular path, they are drawn out of the chamber and collected as fines. Jet-mills do not impact the powder with machinery; they rely on high energy particle-particle collisions to mill the powder. As a result, jet-milling can readily mill rice to small micron diameters. See, e.g., Jeong, E. L. et al., Effect of particle size on the solubility and dispersibility of endosperm, bran, and husk powders of rice. *Food Science and Biotechnology* 2008, 17, (4), 833-838.

Most air-classifiers operate on the same principles as jet-milling. Particles with a large drag force and a small moment of inertia (e.g. protein bodies) are selectively drawn out in the fines stream. Unlike the jet-mill, the particles do not collide because a second stream is added to remove the heavier particles (the coarse stream). Particle separation depends on three factors: particle density, shape, and size. The separation of particles is improved as the difference in particle diameter between fine particles and coarse particles is increased. Experimenters commonly use laser diffraction, scanning electron microscopy, and combustion protein assays (e.g., ELEMENTAR instrument) to characterize the physical properties of cereal starches. Laser diffraction uses laser diffraction patterns produced by a dispersion of particles to estimate the volume distribution of the particles rather than the shape of the particles. Even so, if the particles can be approximated as spheres, the volumes can be used to estimate the particles' equivalent spherical diameter. This statistic gives a rough estimate of the average size of a particle in the powder. One main strength of this technique is its rapid quantitative analysis of a large sample of particles. See, e.g., Stoddard, F. L., Survey of starch particle-size distribution in wheat and related species. *Cereal Chemistry* 1999, 76, (1), 145-149; Kim, W. et al., Effect of heating temperature on particle size distribution in hard and soft wheat flour. *Journal of Cereal Science* 2004, 40, (1), 9-16.

The isolated starch granules can then be incubated with a gas or vapor in order to induce cleavage of the gas-phase cleavable linker situated between the fusion carrier and protein or peptide of interest. Such incubation can be performed by one skilled in the art of exposing animal or plant particles to chemical treatments in dry gas form, such as used in grain fumigation. In one embodiment the particles bearing the protein of interest are incubated in a flow-through cartridge or air column (See FIG. 12). In this embodiment, the gas-phase cleavage linker consists of but is not limited to Asp-Pro, Gly-Thr, Gly-Gly, Met, Ser, Trp, Asn-Gly.

In one specific embodiment, the gas-phase linker sequence is Asp-Pro. Following cleavage, the protein of interest is liberated from the starch granule surface and can be easily captured. The anhydrous process protects the protein of interest from all aqueous based proteases, provides a cost advantage and limits environmentally damaging waste that is associated with conventional aqueous purification methods.

For embodiments of the invention wherein the recombinant fusion protein is to be expressed and purified from starch granules located in plant seed, the DNA expression cassette will include, in the 5' to 3' direction, promoter and 5'UTR sequence capable of expression and localization in plant seeds, a second DNA sequence encoding a carrier protein capable of localizing the recombinant protein to the starch granule surface, a gas-phase cleavable linker and the protein of interest followed by a 3'UTR and terminator sequence functional in plants. In other embodiments the protein of interest is placed upstream of the linker followed by the carrier protein encoding element.

Of particular interest for transcription and translation in plant species, DNA encoded sequences for targeted expression into the seed endosperm tissue can be obtained from rice, wheat, corn, barley, oat or soybean. The required regions for expression of the tethering/anhydrous-cleavage cassette in plant seeds are found in seed storage proteins, starch regulatory proteins or defense proteins. The DNA regulatory sequence (promoter) will be from a gene expressed during seed germination and early stage seedling development, specifically a promoter sequence from the glutelin, globulin, zein or prolamins.

For production of recombinant proteins in algal chloroplasts, a promoter would be chosen to provide maximal expression in said host. The DNA regulatory sequence (promoter) will be from a gene highly expressed in chloroplasts, photosystem A and photosystem B.

This gas phase treatment of biological particles previously tethered with fusion proteins is novel. In this novel process of Dry Fission (or Dry Phission for production of Pharmaceutical proteins) the sample is never exposed to liquids, reducing exposure to proteases and reducing costs for process buffers. Therefore, because of the size of dry proteinated granules and their heavy weight neither open liquid column chromatography type reaction columns or chambers, nor liquid batch vessels for the solid support is necessary to retain the sample in a liquid reaction vessel. However, this tethering fusion protein process still affords the user the option of treating the proteinated granule feedstock of particles with classical down-stream protein purification and polishing methods that are liquid based.

In one embodiment of the novel gas phase cleavage process described herein, the primary requirement for preventing sample loss is a means of protecting the fusion polypeptide from being dislodged from the proteinated granule or particle by excessive mechanical shearing forces such as the gentle Stage One aeroabrasion air flow and Stage Two cleavage gas (which liberates the protein of interest from the granule) that flow past the granule (See, FIG. 12). This requirement is met by placing the particles in an up-flow chamber whose floor is a suitable sized filter such as a fritted glass disc.

Other methods for treating fusion proteins involve embedding the granules in a thin film of Polybrene dispersed on a porous glass disc. For example, the disc may be comprised of a fritted disc of glass (Altosaar, 1956, Patent CA 529624). In another embodiment the starch granules can be entrapped in a mesh of overlapping fibers, held transversely across the reaction chamber allowing the air flow (Stage 1) and the cleavage gas flow (Stage 2) to surround and percolate through the bed of beads (FIG. 12). This structure possesses a relatively high total surface area (hence allowing maximal air-cleaning of the starting particles and maximal interaction of cleavage gas with the surface area of the proteinated granules) with a minimum dimension in the direction of fluid flow. It is known to those skilled in the art of exposing solid proteins to gas phase reactions that the Polybrene film is readily permeable to the reagent vapors so that flowing gases can diffuse into and out of the film to carry out chemical reactions or extractions without mechanically disturbing the sample. The Polybrene forms a cohesive film that adsorbs strongly to the porous glass disc and because of this property the proteinated granules are even further insoluble if user opts to perform liberation of the protein of interest with liquid extraction solvents.

One important characteristic of the fusion protein reaction chamber or cartridge (See FIGS. 7, 11, 12) built around the particle support disc is the ease with which the sample containment area can be miniaturized. This, along with the simple flow-through nature of the cartridge assembly, allows the particle polishing air flow, as well as the peptide bond cleavage gas phase reagent to consume much less of that used in previous commercial instruments for releasing and capturing recombinant proteins. Several benefits of host proteome removal from proteinated granules by aero-abrasion in such vessels or cartridges, and several benefits of dry-fission of recombinant proteins from carrier proteins like puroindoline are well worth noting. The first is a significant reduction in operating costs.

A second is the increased practicality of providing the required amounts of ultrapure cleavage reagent, an important consideration since many of the commercially available chemicals such as enterokinase enzyme for cleaving peptide linker regions require additional purification to provide the desired level of purity.

Yet a third advantage is the increase in speed with which the recombinant protein samples can be cleaved and captured. This is, in part, a result from the decreased time required for mass transfer in the miniaturized system and from the very rapid changeover from one sample of proteinated granule batch to another. Cycle time for gas cleavage can be as short as only 45-55 min, and particle batch reloading (including cartridge cleanup and Polybrene precycling) is only 3-4 h.

Finally, the lower reagent usage per gas phase cleavage cycle results in a reduced accumulation of impurities (endogenous host protein fragments) accompanying the granule-derived samples that are captured downstream. Low background levels of the dry fission recombinant protein process and this miniaturization of artifacts is essential to many applications where recombinant proteins are employed at ultramicro levels. The efficiency with which this new process performs purification of recombinant proteins or peptides is many fold higher than existing art.

The following examples are offered by way of illustration and not by limitation.

Example 1: Isolation of Transgenic Plant Seed Starch Zranules and Anhydrous Purification of the Recombinant Protein of Interest Isolation of seed starch granules is done by first milling the seed into fine flour using a hammer mill, ball mill or elbow-jet mill. This processed flour containing starch granules, protein bodies and cell wall debris can be separated based on size and density using air-classifier or air-cyclone technologies, resulting in a starch granule fraction harboring the recombinant fusion protein on its surfaces. The gas-phase linker (Asp-Pro) can be cleaved by incubating the starch granules with a vapor of heptafluorobutyric acid at 60° C. for 18 hrs. The liberated protein of interest can be collected in an inert air flow and captured on a filter, or isolated through an additional air-classification or air-cyclone step.

Example 2: Isolation of Algal Chloroplast Starch Granules and Anhydrous Purification of the Recombinant Protein of Interest Isolation of algal chloroplasts is done using a density gradient or a hydrocyclone. The isolated chloroplasts are sheared using sonication and the starch granules within can be subsequently isolated using starch granules' distinctive buoyant density, i.e. a sucrose gradient or hydrocyclone. The isolated starch granules are dried to a moisture content of 25% or less using a dryer and incubated with 0.2% heptafluorobutyric acid vapors at 60° C. for 18 hrs. The liberated protein of interest can be collected in an inert air flow and captured on a filter, or isolated through an air-classification or air-cyclone step.

Cultures of algae transformed by the gas-phase cleavable linker-protein of interest (GPCL-POI) expression cassette are dried into cellular powder and then mechanically ruptured by air abrasion (particle-particle collision in air jet mills) and air classification techniques to expose the algal starch granule to gas-phase cleavage.

Example 3: Purification of E. coli Expressed Recombinant Proteins by Starch Granule Binding and Dry Fission Recombinant proteins can be expressed using E. coli, yeast, insect or mammalian cell lines. Expression of recombinant proteins as puroindoline fusions in these hosts will allow for their batch purification using starch granules as affinity beads. The addition of starch granules to the expression slurry of any host cell platform harboring puroindoline fusions will result in the binding of the recombinant protein:: puroindoline fusion onto the starch granule surfaces. The starch granules can then be isolated from the endogenous host proteome and cellular debris using prior art such as batch decanting, gradients, filtration or centrifugation technologies. These starch granules can be rigorously washed with sterilized water or buffers to ensure removal of any loosely bound endogenous host proteins and/or cell debris. The isolated starch granules harboring this recombinant fusion protein on their surfaces can be dried carefully in air (See FIG. 7, 11, 12) or under vacuum and subjected to dry fission using the scissile peptide bonds described above as specified in this DryPhission process, cleaving the recombinant protein (cargo) from the puroindoline fusion carrier, liberating it from the starch granules (See FIGS. 7, 11, 12) for downstream capturing by methods know to one skilled in the art of trapping dry protein powders.

Figure 4:
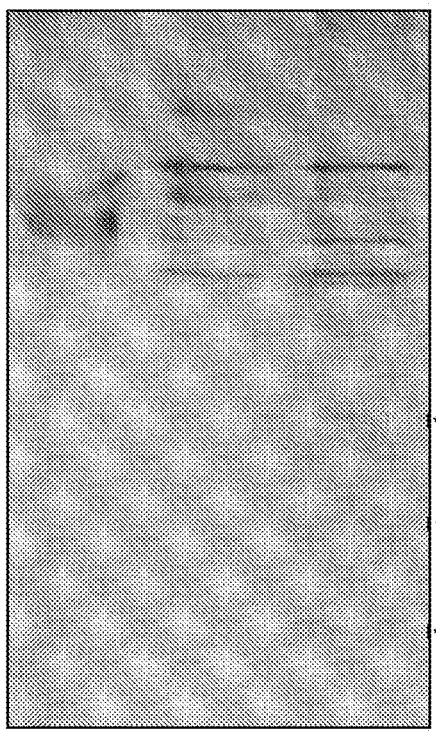
Figure 5:
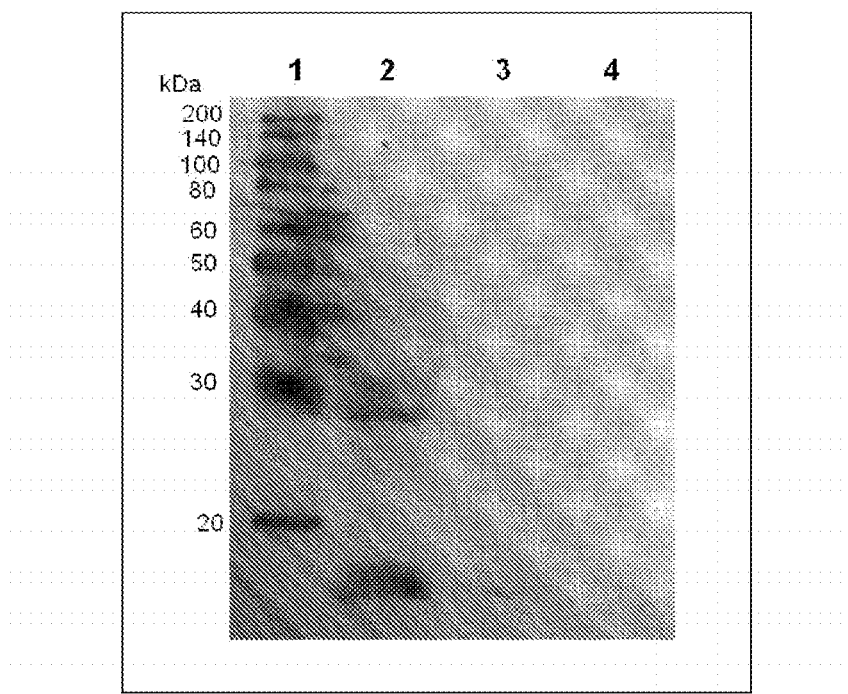

Example 4: Flexible Placement Options for Positioning Carrier and Cargo Domains for Tethering and Subsequent as Phase Cleavage The fusion protein construct can be designed with several possible orientations wherein the carrier is upstream of the cargo domain (e.g. PIN-Asp-Pro-POI), downstream of the cargo domain (POI-Asp-Pro-PIN) or even interspersed within the sequence of the protein of interest (POI), the latter case producing two domains or useful subunits of the POI upon dry fission cleavage [amino-terminal domain of POI-Asp-(Pro-PIN Carrier-Asp)-Pro-carboxy-terminal domain of POI]. It will be obvious to one skilled in the arts of protein chemistry that upon cleavage with a gaseous scissile agent like trifluoroacetic acid that cleavage of such peptide bonds will yield biosimilars wherein the protein of interest may have an adventitious prolyl residue at its amino terminus, or an aspartyl residue at its carboxyl terminus, as the case may be. It is known in the art that such single amino acid residue changes often add stability to and increase the biological activity of recombinant biologics compared to the native wild type protein sequence. It will also be clear to one skilled in the arts of protein hydrolysis that such domain juggling can be an advantage to catalyzing scissile bond cleavage in a sequence specific manner whereby nearest neighbor effects of POI or carrier sequence residues influence the susceptibility of the gas phase linker to rapid and more specific cleavage. As is the case with many of the genomic and proteomic techniques, the large biodiversity of protein sequences in nature means that each construct prepared for granule tethering and gas cleavage will be able to take advantage of such sequence-specific catalysis enhancement.

In another embodiment the carrier domain can comprise any tethering sequence that functions to bind the fusion protein to the target biological particle of choice. For example the tryptophan rich domain of puroindoline-a or -b can contain 5, 7, or more amino acid residues and fusion constructs with such truncated or engineered carriers can be placed downstream of any endosperm-specific promoter to achieve expression in seeds.

Example 5: Isolated Proteins Containing Scissile Peptide Bonds Like Asp-Pro are Cleaved by Exposure to Acidic Gases The usefulness of dry rice flour as a high-throughput food-grade platform involves convenient and inexpensive features such as the ease of determining optimal anhydrous peptide cleavage conditions by varying factors such as volume and concentration of gaseous reagents, length and temperature of incubation, moisture content and mass of rice flour or other chosen biological particles as tethering medium. Anhydrous TFA will cleave Asp-Pro bonds within proteins associated with starch granules isolated from rice. Anhydrous cleavage can be observed readily by exposing model proteins containing the labile Asp-Pro bond to gaseous TFA. The model proteins catalase and tyrosinase were obtained from Sigma-Aldrich (St. Louis, Mo., cat. nos. 120E-7160 and 29C-9640, respectively). Catalase (2 mg) and tyrosinase (2 mg) were weighed and placed into separate microcentrifuge tubes (1.5 ml).

The gas-cleavage apparatus developed in this example was a novel modification of the Solid-Phase nucleic acid polymer synthesizer, comprising of a filter packed in the bottom of a glass reaction vessel (See FIG. 7). Samples of model proteins were loaded on to the filter, where the gas passage can occur. The reaction vessel is connected to a line of tubing that enables a flow path for the gas reagents. The samples were treated with inert nitrogen gas prior to exposure of gaseous TFA. The nitrogen gas flow removes the loosely associated starch granule associated proteins. Samples were then exposed to gaseous TFA for 16 hours and incubated at room temperature. TFA (5 μl) exposed catalase and tyrosinase samples from various incubation periods were placed in 96 well Terasaki Plate (Alpha Biotech Ltd London, UK), in duplicates. BSA standards were also prepared with concentrations ranging from 0.2-2 mg/ml using the Albumin Standard (PIERCE, Ill., USA, #23209). 2504, of Bradford reagent was added to each well. Samples were pipetted up and down and shaken for 30 minutes to mix. Absorbances were read at 595 nm with the PowerWave Microplate Spectrophotometer (BioTek Instruments Inc. Winooski, Vt.). SDS-PAGE gels were run using the Bio-Rad Protein Tetra Mini-Gel System. Samples (4 ug/ul) of model proteins: catalase and tyrosinase exposed to TFA were loaded onto 15% SDS-polyacrylamide mini-gels (8 cm×7.3 cm×1 mm). Concentration of samples was determined by Bradford Assay Standard Curve. The protein marker used was 5 μl of the Benchmark Protein Ladder (Invitrogen). The gels were electrophoresed at 120V for 2.5 hours and silver stained using the 1985 protocol by Heukeshoven and Dernick. Model proteins, tyrosinase (2 mg) and catalase (2 mg) were thus exposed to gaseous TFA using the novel, gas-phase cleavage apparatus (FIG. 7) to observe anhydrous peptide cleavage. Each sample was incubated with pure TFA (gas) in the cleavage apparatus for 16 hours at room temperature to permit cleavage of peptides, specifically at any labile Asp-Pro bond in the model proteins. Following incubation, the sample was transferred from the filter paper directly into a microcentrifuge tube (1.5 ml). The remaining TFA was removed from the sample by vacuum, and the proteins were solubilized in 1 ml of Tris buffer. The same procedure was repeated with catalase. A Bradford Protein Assay was performed after TFA incubation to normalize the amount of protein in each sample. Tyrosinase (4 μg) and catalase (zing) were loaded onto a 15% SDS-PAGE gel. The gel was run at 120V for 2.5 hours. The gel was then silver stained to observe anticipated anhydrous cleavage products (FIGS. 4 and 6). Cleavage products of the anticipated masses, as predicted based on the location of the Asp-Pro bonds, were observed for the model proteins, tyrosinase and catalase. As known to one skilled in the art, mass spectrometry is used to elucidate the sequence of the cleavage products and confirm the cleavage occurred at the Asp-Pro site.

Tyrosinase isolated from *Bos taurus* is an 80 kDa protein consisting of two Asp-Pro cleavage sites. With the presence of two Asp-Pro cleavage sites, three cleavage products are predicted. Based on the amino acid sequence (GenBank: AAL02331.2), the expected peptide sizes are 11, 20, and 49 kDa. Upon five minute exposure to pure, gaseous TFA using the novel anhydrous cleavage apparatus, cleavage of tyrosinase was observed, and indicated by arrows (See FIG. 4). The right hand lane in the silver stained SDS-PAGE gel showed the presence of three cleavage products, as three faint bands were observed (See FIG. 4). Three cleavage products were expected during anhydrous cleavage of tyrosinase at the Asp-Pro bond. Since a very little quantity of protein was loaded (4 μg), it is expected that the bands may not be as visible with heavier protein sample applications. Higher concentrations of protein allow one to observe more distinct cleavage products. Middle lane represents a control sample of tyrosinase, unexposed to gaseous TFA. It is therefore expected that cleavage products be absent in the center lane. The multiple faint bands of higher Mr in the center and right hand lanes may indicate low purity of the tyrosinase protein sample or different possible isoforms. It is expected that one band at 80 kDa can be identified as tyrosinase using western blotting or mass spectrometry of the gel slice. Left hand lane represents 5 μl of the PageRuler protein Ladder. The PageRuler Ladder underwent some degradation and thus the 10 bands that were expected to be observed are absent. The 85 kDa band was the only band present. Since the Benchmark Protein Ladder is not observed in the left lane, it is difficult to assign accurate sizes to the cleavage products in the right lane. However, the migration distance of the cleavage products on the gel corresponds to the predicted peptide sizes of 11, 20 and 49 kDa.

Anhydrous Cleavage of Catalase is another model system that exemplifies the power of particle tethering of fusion proteins followed by liberation via gas cleavage of the rt Protein. Catalase from *Bos taurus* is a 72 kDa protein containing at least one Asp-Pro cleavage site. The amino acid sequence (NCBI Reference Sequence: NP 001030463.1) shows that an Asp-Pro cleavage site appears approximately in the middle of the amino acid sequence of catalase, therefore two cleavage products of roughly similar sizes are predicted from that scissile bond. The identification of the faint 50 kDa MW band, however, suggests that the band corresponding to the cleavage products may represent the expected sizes of 35 and 37 kDa. Similar to the results obtained for tyrosinase, a 16 hour exposure to gaseous TFA in our anhydrous cleavage apparatus resulted in cleavage of catalase, represented by the red arrow (See FIG. 6). Unlike tyrosinase, the catalase protein is represented by a single band in the SDS-PAGE silver stained gel, indicating a high level of purity (See FIG. 6). One distinct band was observed as a cleavage product in lane 2. This single band is expected to represent two cleavage products of similar masses, which is expected upon anhydrous cleavage of catalase at the Asp-Pro bond. Lane 1 represents a control sample of catalase, unexposed to gaseous TFA. It is therefore expected that cleavage products be absent in lane 1. In order to distinguish between the 35 kDa and 37 kDa cleavage products, a high percentage Tricine-SDS-PAGE gel can be run to resolve the gas cleavage peptides. Tricine-SDS-PAGE is a relatively new technique which is becoming the method for resolving proteins in the 1-100 kDa range preferred by those skilled in the art of protein gel electrophoresis.

What is claimed is:

1. A method for obtaining a protein or peptide of interest from plant material comprising:

(a) providing the plant material comprising a recombinant protein or peptide, the recombinant protein or peptide comprising the protein or peptide of interest, a carrier protein comprising puroindoline, and a gas/vapor phase cleavage site situated between the protein or peptide of interest and the carrier protein, the carrier protein comprising an Asp-Pro sequence, wherein the plant material comprises starch granules that are powdered and at a moisture content of less than 25%;

(b) incubating the plant material with gas or vapors selected from heptafluorobutyric acid, acetic acid, formic acid, hydrochloric acid, anhydrous hydrazine, perfluorobutyric acid, trifluoroacetic acid, fluorosulfuric acid, and perfluoric acid to cleave the gas/vapor cleavage site and release the recombinant protein or peptide from the carrier protein, to produce a released protein or peptide of interest; and (c) separating the released protein or peptide of interest from the carrier protein and the plant material, thereby obtaining the protein or peptide of interest.

2. The method of claim 1, wherein the carrier protein causes the localization and deposition of the recombinant protein on to a surface of the starch granules.

3. The method of claim 1, wherein the starch granules that are powdered are separated from other cellular components using milling, air-classification, air cyclone, or a combination thereof, prior to the step of incubating with the gas or vapor.

4. The method of claim 1, wherein the heptafluorobutyric acid is present at a concentration from 0.05 percent to 20 percent.

5. The method of claim 4, wherein the concentration of heptafluorobutyric acid is 0.1 percent to 5 percent.

6. The method of claim 1, wherein the reaction is at a temperature is from 25 degrees Celsius to 100 degrees Celsius.

7. The method of claim 6, wherein the reaction is at a temperature from 40 degrees Celsius to 80 degrees Celsius.

8. The method of claim 7, wherein the reaction is at a temperature from 55 degrees Celsius to 65 degrees Celsius.

9. The method of claim 1, wherein the incubation of the reaction is from 1 hour to 60 hours.

10. The method of claim 9, wherein the incubation of the reaction is from 10 hours to 40 hours.

11. The method of claim 10, wherein the incubation of the reaction is from 14 hours to 18 hours.

12. The method of claim 3, wherein the protein or peptide of interest is captured from an air flow using a filter device following the step of incubating with the gas or vapors.

13. The method of claim 12, wherein the filter device is selected from glass fibers, quartz microfibers, polybrene, and cellulose.

14. The method of claim 1, wherein the protein or peptide of interest is trapped from an air flow using a dust collection device following the step of incubating with the gas or vapors.

15. The method of claim 1, wherein the protein or peptide of interest is trapped from an air flow using an electrostatic surface-trapping device following the step of incubating with the gas or vapors.

* * * * *

UNITED STATES PATENT AND TRADEMARK OFFICE
CERTIFICATE OF CORRECTION

PATENT NO. : 10,294,268 B2
APPLICATION NO. : 15/027884
DATED : May 21, 2019
INVENTOR(S) : Illimar Altosaar Page 1 of 2

It is certified that error appears in the above-identified patent and that said Letters Patent is hereby corrected as shown below:

In the Specification

Column 1, Line 59, replace "has" with -- have --

Column 1, Line 66, replace "case" with -- ease --

Column 3, Line 59, replace "Scr" with -- Ser --

Column 4, Line 66, replace "anti-PN" with -- anti-PIN --

Column 5, Line 50, delete "a" before "scanning"

Column 5, Line 50, replace "micrograph" with -- micrographs --

Column 5, Line 54, replace "Before Jet-milling" with -- Before Jet-Milling --

Column 7, Line 18, delete "our" before "recombinant"

Column 8, Line 62, replace "photosystem A" with -- photosystem I --

Column 8, Line 62, replace "photosystem B" with -- photosystem II --

Column 8, Line 65, replace "Dry Phission" with -- Dry PhissionTM --

Column 10, Line 20, replace "Zranules" with -- Granules --

Column 11, Line 22, replace "as" with -- Gas --

Column 12, Line 30, replace "2504," with -- 250 µL --

Signed and Sealed this
Eighth Day of October, 2019

Andrei Iancu
*Director of the United States Patent and Trademark Office*

CERTIFICATE OF CORRECTION (continued)
U.S. Pat. No. 10,294,268 B2

Column 12, Line 57, replace "( 4 μg)" with -- (4μg) --

Column 12, Line 58, replace "(zing)" with -- (4μg) --

In the Claims

Column 14, Lines 15-16 (Claim 1), replace "perfiuorobutryic" with -- perfluorobutyric --

Column 14, Line 16 (Claim 1), replace "trifiuoroacetic" with -- trifluoroacetic --

Column 14, Line 38 (Claim 6), delete "is" before "from"